United States Patent [19]
Kume

[11] Patent Number: 5,648,264
[45] Date of Patent: Jul. 15, 1997

[54] THERMOCELLULOLYTIC BACTERIA AND THEIR USES

[75] Inventor: Shigeru Kume, Fukuoka, Japan

[73] Assignee: Gomei Kaisha Nakamura Sangyo, Fukukoka, Japan

[21] Appl. No.: 256,254

[22] PCT Filed: Apr. 16, 1993

[86] PCT No.: PCT/JP93/00498

§ 371 Date: Jun. 30, 1994

§ 102(e) Date: Jun. 30, 1994

[87] PCT Pub. No.: WO94/10290

PCT Pub. Date: May 11, 1994

[30] Foreign Application Priority Data

Oct. 30, 1992 [JP] Japan .................. 4-315835

[51] Int. Cl.$^6$ .............. C12N 1/20; C12N 9/42; C12N 9/52; C12P 39/00
[52] U.S. Cl. .............. 435/264; 71/DIG. 2; 71/9; 422/5; 424/93.41; 435/42; 435/209; 435/220; 435/252.1; 435/252.4; 435/252.7; 435/277; 435/842; 504/117
[58] Field of Search .............. 424/93.41, 71.1, 424/71.6, 71.7, 71.8; 435/252.1, 252.4, 842, 264, 277, 252.7, 209, 220, 42; 71/DIG. 2, 3; 422/5

[56] References Cited

U.S. PATENT DOCUMENTS 4,400,470   8/1983   Zeikus et al. .

FOREIGN PATENT DOCUMENTS

| 27-3174 | 8/1952 | Japan . |
|---|---|---|
| 30-8019 | 11/1955 | Japan . |
| 36-23691 | 12/1961 | Japan . |
| 53-75072 | 7/1978 | Japan . |
| 55-38834 | 3/1980 | Japan . |
| 59-501194 | 7/1984 | Japan . |
| 61-23994 | 6/1986 | Japan . |
| 63-216481 | 9/1988 | Japan . |
| 2-62237 | 12/1990 | Japan . |
| 5-30968 | 2/1993 | Japan . |

OTHER PUBLICATIONS

Applied and Environmental Microbiology, pp. 1337–1343, Jun. 1981, vol. 41, No. 6.
Applied and Environmental Microbiology, pp. 1125–1132, May 1982, vol. 43, No. 5.
Biotechnology and Bioengineering, pp. 92–100, Jan. 1987, vol. 29, No. 1.
Biochemical Journal, pp. 407–413, 1984, vol. 221, No. 2.
Agricultural and Biological chemistry, pp. 25–28, Jan. 1983, vol. 47 No. 1.

*Primary Examiner*—Herbert J. Lilling
*Attorney, Agent, or Firm*—McAulay Fisher Nissen Goldberg & Kiel, LLP

[57] ABSTRACT

*Clostridium thermocellum* biovar. nov. SK522 (FERM BP-345 g) is a thermophilic cellulose decomposing bacteria, capable of solubilizing lignin and fermenting cellulose excellently. Although its temperature limit for growth is 40°–80° C., it grows best at 65°–72° C.

*Thermus aquaticus* biovar. nov. SK542 (FERM BP-3382) is an absolute aerobic bacteria. It grows at temperature limit of 40°–82° C. in a normal concentration medium, but its best growth is achieved at 72°–76° C. It produces protein decomposing enzymes functional at a temperature of 75°–85° C. and active in a wide pH range of 4.0–11.3, and a yellow pigment of carotenoid groups.

Both strains can be mix-cultured. Depending on various purposes, as the mix culture is able to decompose organic materials containing cellulose and/or lignin, it can be used for soil improvement.

18 Claims, No Drawings

THERMOCELLULOLYTIC BACTERIA AND THEIR USES

TECHNICAL FIELD

The present invention relates to new bacteria capable of decomposing celluloses and their usage, especially, in relation with their agricultural usage in soil improvement. In more detail, the present invention relates to the bacteria useful for solubilizing natural lignin, fermenting and decomposing wood and other cellulosic materials difficult to be decomposed, proteinaceous substances and sludge, producing manure and compost, accelerating the maturity of humus as a product of decomposable biomasses, improving soil fertility and soil structure and techniques related to those available for practical uses.

BACKGROUND TECHNIQUES

In agricultural and other industrial fields, a large amount of hard-decomposable organic materials or hard-decomposable cellulosic substances, for example, sawdust, chipdust, pruner waste, bark, other lumber industrial products such as scrap wood, chaff, rice straw, wheat straw, hull and seed coat of beans such as soybean, red bean and peanut, coffee dregs, fallen leaves, bark, reed and mountain grass of miscanthus, discarded parts of shiitake (*Cortinellus shiitake*) and other mushrooms, and other plant materials having C/N ratio of 40-100% or more are discarded.

Although they are composed of extremely complicated organic components, in general the essential components are about 30-75% cellulose and 15-40% lignin. When both are combined, they occupy, in majority, more than 45-90%. The nexts are hemicellulose 7-25% and those present in a small amount such as nitrogen-containing compounds such as proteins, sugars, organic acids, alcoholic compounds. Moreover, fat, wax and essential oil are also present.

If the above-mentioned plant materials can be decomposed efficiently, the efficient uses of the discarded materials can be profitably used, and, they can be used as organic fertilizers. Moreover, as the above-mentioned plant materials can be applied to soil, if they can be decomposed efficiently, they can be a useful soil-improvement agent.

As most of plant materials contain lignin and cellulose, for efficient decomposition of plant materials, a means for efficiently decomposing and solubilizing lignin and cellulose is essential. However, by using existing microorganisms and enzymes as decomposers, quick decomposition of cellulose or solubilization of lignin is extremely difficult. Furthermore, the enzymes do not act on hard proteins such as gelatin and collagen either. As a consequence, the effective decomposition and solubilization of natural hard-decomposable organic materials by microorganisms have not been successful so far.

Therefore, the present invention provides new bacteria that can excellently ferment celluloses and solubilize lignins, a culture mixture whose abilities are improved, a process for decomposing hard-decomposable substances, methods of soil improvement, production of organic fertilizers, and deoderization of excreta.

DISCLOSURE OF INVENTION

Accordingly the present invention provides a bacterium *Clostridium thermocellum* biovar. nov. SK522 (FERM BP-3459) capable of excellently decomposing cellulose, growing at temperature range of 40°-80° C., with best growth at 65°-72°, capable of solubilizing lignin, and any bacteria having the same properties.

The present invention further provides a bacterium *Thermus aquaticus* SK542 FERM BP-3382) producing yellow carotenoid pigment and protein-decomposing enzyme which functions within a pH 4.0-11.3, being active at temperature of 75°-85° C., growing within a temperature limit of 40°-82° C. in a culture medium of regular concentration, having a growth suitable-temperature of 72°-76° C. and having good properties, and other bacteria possessing the same properties.

The present invention further provides a mixed culture obtained by co-culturing the above-mentioned two bacteria.

The present invention also provides a method for solubilizing lignin characterized by acting said mixed culture on organic materials containing lignin.

The present invention further provides an organic material-decomposing agent comprising said mixed culture and an additive.

The present invention provides a method for improving solid characterized by applying said mixed culture or said organic material-decomposing agent to soil.

The present invention further provides a process for production of an organic fertilizer characterized by activating said mixed culture or said organic material-producing organic fertilizer which is a distinctive decomposing agent to an organic material containing lignin and/or cellulose.

The present invention still more provides a method for decorating excreta characterized by acting said mixed culture or said organic material decomposing agent to excreta.

DETAILED DESCRIPTION

First, microorganisms of the present invention are explained.

The microorganisms utilized in the present invention are new bacteria, SK522 and SK542, and strains having the same properties thereof. The various properties of both bacteria are as set forth hereinafter.

Note that experiments on the following taxonomical properties and identification are all conducted according to the Bergey's Manual of Determinative Bacteriology 7th edition (1951), 8th edition (1974) and the Bergey's Manual of Systematic Bacteriology Vol. 1 (1984) and Vol. 2 (1986).

(I) Strain SK522

(*Clostridium thermocellum* biovar. nov. SK522, FERM BP-3459)

Taxonomical Properties The microorganism can not grow without associating bacterium. However, since the associating bacterium can easily grow in single-separate pure culture, the microorganism and associating bacterium were cultured and several properties were tested in this condition.

Shape The microorganism has a rod-like shape, but a slightly curved shape is also present. It grows singly, but sometimes it couply grows. 0.3 to 0.5×2.2 to 4.0 micron. In aged culture, they are stretched and form a chain-like shape, 5.7-12.8 micron long. Peritrichous, in a dropculture at room temperature, the movement thereof can not be seen. It forms spores having oval or circular ends, the cells are swollen and form a cylindrical shape.

It is gram negative.

Cultural properties (1) Plate Culture

The microorganism does not grow in a plate culture and other conventional media. However, the present strain forms yellow-spotted colonies with associating bacterium on a round-shape filter paper agar plate, as Viljoen et al. described, but the microorganism can not grow alone.

(2) Slant Culture, Stab Culture

In a slant culture on agar medium of the filter paper of Viljoen et al. treated with Schweizer reagent, or in a stab culture using the same medium, the microorganism cannot grow.

(3) Potato culture, Gelatin Culture

The microorganism can not grow by surface culture and stabbed culture.

(4) Liquid Culture

Only in Viljoen et al. medium, and media which contain cellulose, such as aqueous cellulose peptone (less growth), cellulose bouillon can, its growth be recognized. If carbon sources are substances other than cellulose, such as glucose and xylose, its ability on decomposing cellulose will be lost.

Physiological and Biochemical Properties.

(1) Enzymatic Action etc.

(1) Cellulose Decomposition

The cellulose decomposing enzymes of the present bacterium are essentially a mixture of β-1, 4-glucanases. It is extracellularly secreted, the functioning temperature being more than 80° C., heat resistant at pH more than 10.0, and some are alkali resistant. The enzymes cut macromolecule of cellulose of micell contraction from its end, and, glucose, cellobiose and cellooligo saccharides are formed.

The followings show a list of basic properties relating to its enzymatic substrates.

| | | |
|---|---|---|
| Decomposition of filter paper | FP-ase | positive |
| Decomposition of Avicell | Avicellase | positive |
| Decomposition of cellobiose to 2 molecules of glucose | Cellobiase | positive |
| (2) Lignin Decomposition | | |
| Solubility of rice straw lignin | | positive (Weak, slighly weak) |
| (3) Decomposition of protein | | |
| Proteolytic enzymes | | negative |
| Peptidase | | negative |
| (4) Hydrolysis test of starch | | slightly positive |
| (5) Hydrolysis of hemicellulose, xylane, pectin | | negative |
| (6) Invertase, maltase | | positive |
| (7) Decomposition test of fat | | negative |
| (8) Oxidation reaction | | |
| Hydroquinon reaction | | positive |
| Tyrosin reaction | | negative |
| (9) Reducing action | | positive |

2. Product Test (1) Cellulose Fermentation

Fermentation ratio of 78–91%, cellulose is excellently fermented, and ethanol, methanol, acetoaldehyde, acetate, lactate, formate, butyrate, succinate, fumarate, tartarate, gluconate, glucose, cellobiose, celboligosaccharides, cellodextrin, large quantity of carbonate gas, hydrogen and hydrogen sulfide are produced.

(2) Products from sugars and alcohol

Acids are formed from glucose, sucrose, maltose and cellobiose.

(3) Gas generation test

From cellulose, gas is intensely produced. However, from glucose, sucrose, maltose, cellobiose, gas production is not recognized.

| | |
|---|---|
| (4) Pepton water test | |
| Ammonia | slightly reaction |
| Indole | positive |
| Skatol | positive |
| Hydrogen sulfide | positive |

(5) Pigment production

In general, carotenoid yellow pigment is formed.

3. Growth Condition (1) Growth temperature

The most suitable temperature is 65°–72° C., temperature limits are 40°–80° C., at lower than 40° C. it does not grow.

(2) Hydrogen ion concentration (pH)

The most suitable pH range is 6.7–8.0, pH limit is 5.6–9.6.

(3) Nitrogen source

The best source is peptone, but urea, asparagine, sodium glutamate are still good nitrogen sources. Ammonium salt is a good inorganic nitrogen source.

(4) Carbon source

If it is continously subcultured in hydrocarbons other than cellulose, its ability of growth and fermentation will be lost.

(5) Oxygen effect

By testing at Eh=–200 to –250 mV, it is grouped into anerobic bacteria.

(6) Micronutrient requirement

Biotin, pyridoxamin, vitamin $B_{12}$, p-amino benzoate are required.

(7) Content of DNA's G+C

The mol % of G+C is about 38–40 (Tm).

Taxonomical Position

Having the most suitable growth temperature of 65°–72° and temperature limits of 40°–80°, the followings are thermocellulolitic bacteria capable of excellently fermenting cellulose similar to strain SK522.

*Clostridium thermocellum* (Viljoen, Fred and Peterson, 1926. Jour. Agric. Sci. (London), 16, 7 (1926)

*Clostridium dissolvens* (Bergey et al. 1925, alias *Bacillus cellulose dissolvens* Khouvine, 1923.: Ann. Inst. Past. 37, 711 (1923); Bergey's Manual, 2nd. Ed. (1925) p. 344.

*Clostridium thermocellulaseum* Enebo, 1951.: Bergey's Manual, 7th. Ed. (1957) p. 689.

*Bacillus thermocellulolyticus* Coolhaas. 1928.: Cent Bakt. II, 75, 101 (1928), 76, 38(1929).

*Bacillus thermofibrincolus* Itano and Arakawa, 1929: Agricultural Chemistry 5. 816, 921 (1929); 6, 248, 257 (1930).

Agricultural Chemistry, 5. 816, 921 (1929); 6, 248, 257 (1930).

Among them, *Clostridium dissoluens* is most similar to the present strains in morphological, cultural and physio-biochemical tests except the following 4 points.

(1) It is capable of solubilizing lignin weakly or very-weakly.

(2) The optimum growth temperature is 65°–72° C., growth temperature limit is 40°–80° C. At a temperature lower than 40° C., it does not grow.

(3) It is capable of excellently fermenting cellulose, but incapable of fermenting hemicellulose, xylan, pectin.

(4) The ability for solubilizing lignin is remarkable in the presence of a microorganism belonging to the genus Thermus, and at the same time, it has a good influence on the ability for cellulose decomposition of the present strain and other functions as well.

However, in the Bergey's Manual of Systematic Bacteriology Vol. 2 (1986) p. 1104 and 1141, only *Clostridium thermocellum* is described as thermophilic decomposing bacterium. *Clostridium dissolvens* and others are considered as a subspecies or variant of *C. thermocellum*, or suspected as an imperfect experimental result.

Therefore, the classification of the present strain was conducted by comparing it with taxonomical properties of *Clostridium thermocellum*, at the same time, comparing with other thermocellulolytic bacteria.

As described above, when morphological properties were compared, and the results were summarized, the distinctively characteristical differences of the present strain from *Clostridium thermocellum* and those of the above-mentioned thermophilic cellulose-decomposing bacteria are, in addition to the above-mentioned 4 points of differences, in the functions against carbohydrates, micronutrient requirement and other problems, and especially those related to lignin, were emphasized.

The strain has an ability to solubilize lignin. That ability can be remarkably increased if it is co-cultured with *Thermus aquaticus* strain SK542. Unfortunately, description relating to decomposition of lignin by *Clostridium thermocellum* and thermocellulolytic bacteria are not completely available. Even if it is available, it relates to an inhibitory function concerning cellulose decomposition.

Based on such reasons, and considering the physio-biochemical properties for lignin solubilization of the present strain, the new strain was named *Clostridium thermocellum* biovar. nov. SK522.

Deposition Number

The deposition number of the present strain is FERM BP-3459. The strain is characterized as a deposited new strain based on a standard strain, belonging to *Clostridium thermocellum* Viljoen, Fred and Peterson (1926), having an ability for solubilizing lignin, its ability on solubilizing lignin will be remarkably increased if the strain is mix-cultured with bacterium belonging to the genus Thermus Brock and Freeze 1969. The present strain is a new strain on the basis of physio-biochemical characteristics covering strain SK522, and natural and artificial mutants.

Screening of Strain SK522

Using as an isolation source, soil, coastal mud, compost, human, household and animal nightsoils, enrichment culture is repeated several times at 55°–65° C., and isolation is conducted with a filter paper-agar slab culture of Tetrault as suggested by Viljoen et al.

Nutrients which are contained in Vijoen et al.'s medium are enough, but it will be better if inorganic metal salts, vitamins, growth promoting factors, for example yeast extract, are added. The medium of Viljoen et al. (Viljoen, Fred and Peterson, 1926).

| | |
|---|---|
| Peptone | 5.0 g |
| Calcium carbonate | saturated |
| Sodium ammonium phosphate | 2.0 g |
| Potassium phosphate | 1.0 g |
| Magnesium sulphate | 0.3 g |
| Calcium chloride | 0.1 g |
| Iron (II) chloride | Trace |
| Cellulose (filter paper) | 15.0 g |
| Well water | 1000 ml |

Usefulness of Strain SK522

Strain SK522 is a very excellent cellulolytic bacterium. There are two strain types, weak and very weak ones. As they also have an ability to solubilize lignin, when they are mix-cultured with bacterium of genus Thermus, their ability especially cellulolytic ability will be remarkably increased.

Moreover, those increased ability in a mix culture may be used for decomposing various cellulose materials. As a consequence, a method of compost production will be advanced, and a method of compost production with a high rate decomposing process can be established. Furthermore, by using strain SK522 and SK542, soil microbial flora will be healthily activated, the growth of useful bacteria having an ability of buffering against environmental changes and their useful effects will be maintained, and soil-born diseases and other problems resulted from continuous cropping can be eliminated. In addition, the development of technology on applying them to soil and plant leaf surface, deodorization of excreta, decomposition of hard-proteinaceous substances, as new methods of microbial usages, can be expected.

(II) Strain SK542

(*Thermus aquaticus* biovar. nov. strain SK542, FERM BP-3382)

Taxonomical Properties

Shape Rod-like, 0.4–0.6×3.0–5.0 micron long. It is affected by medium condition, for example as the culture becomes aged, it is thready-like, 20–130 micron long. It does not have flagellum. At room temperature, its movement is barely recognized. It also does not have end spores and is gram negative.

Culturing Properties

It vigorously grows with generation time of 20–50 minutes.

(1) Plate Culture

3% agar, 60° C.: yellow, comparatively minute, small circular colonies.

(2) Agar Stab Culture

Surface growth only, yellow, merely enlarged.

(3) Liquid Culture

Surface coating growth (stationary culture)

Physio-Biochemical Properties

1. Enzymatic Actions

| | | |
|---|---|---|
| (1) | Protein Decomposition | |
| | Proteolytic enzymes | positive (strong) |
| | Gelatin hydrolysis | positive |
| | Peptidase | positive |
| (2) | Starch hydrolysis | slightly positive |
| (3) | Pectin hydrolysis | positive (weak) |
| (4) | Cellulose decomposition | negative |
| (5) | Lignin decomposition | negative |

Eventhough both cellulose and lignin decompositions are negative, in a mix culture with thermocellulolytic bacterium SK522, it remarkably increases the ability of the strain SK522 to solubilize lignin, and at the same time, cellulose decomposition ability and other functions are positively affected.

| | | |
|---|---|---|
| (6) | Fat decomposition | negative |
| (7) | Invertase, maltase | positive |
| (8) | Catalase, oxidase responses | positive |
| (9) | Hydrogen sulfide formation | positive (weak) |
| (10) | Sulfuric acid reduction reaction | negative |
| 2. | Product Test | |
| (1) | Production of acid and gas from sugar and alcohol | |
| | It does not produce gas, but produces acid from glucose, galactose, maltose, lactose and glycerol. | |
| (2) | Indole and skatol formation | negative |

It produces yellow pigment (carotinoid pigment, the muximum absorbance 450 nm and small peaks at 430, 435 and 470 nm). However, in a mix culture with glucose and other sugars as carbon resources, it does not produce pigment.

3. Growth Condition (1) Culture concentration

Bacteria belonging to the genus Thermus are generally sensitive to the concentration of organic substances. If the nutrient requirements are low, low concentration should be used. However, the present strain responds differently as even with normal concentration it can grow well.

It can also grow with more than 5% NaCl, even though the optical concentration is between 2.0–3.0%. In general, however, bacteria belonging to the genus Thermus can not grow in the presence of more than 2% NaCl.

It grows also with more than 3% Na-glutamate and more than 5% sucrose or maltose. Even 2% peptone+1% yeast extract can not interfere its growth. In general, bacteria belonging to the genus Thermus grow suitably in the presence of approximately 1% of each tryptone and yeast extract, but if their concentrations are increased each more than 1%, the strain can not grow.

(2) Growth temperature

The optimum temperature is between 72°–76° C., and growth temperature range is 40°–82° C. It can not grow below 40° C.

(3) Hydrogen ion concentration (pH)

The most suitable pH is between 6.0–10.0. Growth pH range is 4.0–11.0.

(4) Nitrogen source

Protein of gelatinous materials, glutamate salts, urea, and inorganic nitrogen, especially ammonium salts are frequently used.

(5) Carbon source

Glucose, sucrose, maltose, galactose, cellobiose, raffinose, stachyose, starch, glycerol, acetate, butyrate, malate, glutamate salts are used.

(6) Effects of $O_2$

The strain is absolutely aerobic.

(7) Micronutrient requirement

Its micronutrient requirement is high. Biotin, nicotinate amide and thiamine are important. However, for the good growth, it needs metal ions such as Fe, Mn, Ca in comparatively high concentration. In addition, it is susceptible to the amount of those minerals.

(8) Sensitivity to antibiotics

In general, bacteria belonging to the genus Thermus and those similar to it are very sensitive to Penicillin G, Chlororamphenicol, Tetracycline, Streptomycin, Kanamycin and other antibiotics.

(9) Content of DNA's G+C

It is estimated that the mol % of G+C=68 (Tm).

Taxonomical Position

The present strain is absolute aerobic, its optimum growth temperature is between 72°–76° C., growth temperature range is 40°–82° C., and it does not grow under 40° C. Because it is asporogenous, gram negative bacillus, and based on other many mycological properties, the strain is identified to belong to the genus Thermus Brock and Freeze (1967). Moreover, if bacteria resembling to genus Thermus are considered, such as *Thermus aquaticus* Brock and Freeze 1969 (Bergey's Manual, 1984, Vol. 1, p. 337), *Thermus thermophilous* Oshima and Imahori 1974 (Int. J. Bacterial., 24, 102, 1974) and *Thermus flavus* Saiki, Kimura and Arima 1972 (Agr. Biol. Chem., 36, 2357, 1972), the only species belonging to the genus Thermus Brock and Freeze (1967) in the present Bergey's Manual of Systematic Bacteriology Vol. 1 (1984) p. 333 is *Thermus aquaticus* Brock and Freeze 1969. Moreover, as the distinctive characteristics mentioned below are not found among the well-known species, it has been identified as a new strain of *Thermus aquaticus*, *Thermus aquaticus* biovar. nov. SK542.

(1) In a mix culture with thermocellulolytic bacterium, SK522, its lignin solubilizing ability is remarkably increased. At the same time, its cellulose decomposing ability and other functions are preferably affected.

(2) It has a strong ability for decomposing protein in a wide pH and temperature ranges.

(3) It is different from the species of the well-known genus Thermus, as its susceptibility to the concentration of organic substances is very low, and it grows well even in a medium with normal concentration.

(4) Its requirement on micronutrients is high, it requires vitamins and metal ions. In addition, it is susceptible to the quantity of minerals.

(5) It produces yellow pigment (carotenoid pigment, the miximum absorbance is 450 nm, and small peaks are observed in 430, 435 and 470 nm).

Deposition Number

It was deposited as FERM BP-3382. It is identified according to a standard strain belonging to the genus *Thermus aquaticus* Brock and Freeze (1969). If it is mix-cultured with cellulolytic bacteria (strain SK522), the lignin solubilizing ability will be remarkably increased, and at the same time, cellulose-decomposing ability will be preferably affected. It is a new strain according to physiological and biochemical properties covering natural and artificial mutations and strain SK542.

Screening of Strain SK542

The sources for isolation of strain are humus and soil of hot-spring areas of Kyushu and its neighborhood. After culturing a sample at 55°–60° C., the microorganism is isolated on 3% agar plate culture medium.

Isolating Medium Composition (Castenholz medium: Castenholz, R. W.; Bacterial. Rev., 33, 467 (1969))

| | |
|---|---|
| Nitrilotriacetic acid | 100 mg |
| $CaSO_4.2H_2O$ | 60 mg |
| $MgSO_4.7H_2O$ | 100 mg |
| NaCl | 8 mg |
| $KNO_3$ | 103 mg |
| $NaNO_3$ | 689 mg |
| $Na_2HPO_4$ | 111 mg |
| $FeCl_3$ | 0.28 mg |
| $MnSO_4.H_2O$ | 2.2 mg |
| $ZnSO_4.7H_2O$ | 0.5 mg |
| $H_3BO_3$ | 0.5 mg |
| $CuSO_4$ | 0.016 mg |
| $Na_2MoO_4.2H_2O$ | 0.025 mg |
| (Yeast extract | 5,000 mg) |
| (Triptone | 5,000 mg) |
| (Sucrose | 10,000 mg) |

Total volume (with pure water, pH=about 8) 1,000 ml

Note: The numbers in the parentheses are modifications by the inventors.

Usefulness of Strain SK542

The usefulness of this strain is characterized by the following three actions and functions.

(1) In a mix culture with cellulose decomposing bacterium (strain SK522), its lignin decomposing ability is remarkably increased. Not only its cellulose decomposing ability is increased, but other functions are also preferably affected.

(2) Its protein decomposing ability strongly functions in wide pH and temperature ranges.

(3) It produces insoluble carotenoid yellow pigment. The yellow pigment in a microbial cell becomes a water-soluble, low-molecular weight material by decomposition by other microbes. It is then absorbed by plants and useful for increasing fruit qualities such as fruit taste, luster and storage life. In addition, by applying the cells of strain SK542, those basic properties are multiplied, and the growth of heterotrophic microbes and soil-borned bacteria are stimulated.

Different from well known bacteria belonging to the genus Thermus, the present strain makes ecological and farming systems, various hard-decomposable celluloic substances, scleroprotein, sewage sludge and many organic materials useful, due to its weak susceptibility to the concentration of organic material in addition to the above-mentioned properties.

Moreover, this fact provides an improved productivity, overcoming, soil-borned diseases, problems related to continuous cropping, development of new techniques for deodorizing and decomposing excreta, and direct spreading to soil or leaf surface.

(III) A mix culture of Strain SK522 and SK542

1. Mass-culture of strain SK522

The strain is cultured in a previously mentioned Castenholz medium (Castenholz, 1969) under anaerobic or semi anaerobic condition, at 65°–70° C., for 48–60 hours.

2. Mass-culture of strain SK542

The previously mentioned Castenholz medium (Castenholz, 1969) is used. The strain is cultured under aerobic condition by aeration or shaking, at 70°–75° C., for 24 hours.

3. Mix-culture of strains SK522 and SK542

The medium used is listed below. An appropriate amount of each mass-culture of strain SK522 and SK542 is inoculated, and then cultured at 60°–70° C. for 24–36 hours as a mix-culture of both strains. Then, the culture is made powder using and the water content becomes to less than 5–7%, so that the mixture can resist the storage for more than 2 years. In addition, the mass culture of both strains are taken in same amounts, mixed well, and then used. The culture is processed into powder as the process will not change the culture properties.

The following is the medium E which is used a mix-culture medium.

| | |
|---|---|
| $K_2HPO_4$ | 5 kg |
| $(NH_4)_2SO_4$ | 2 kg |
| Urea | 2 kg |
| Peptone | 5 kg |
| Yeast extract | 5 kg |
| Filter paper (cellulose) | 15 kg |
| $CaCO_3$ | saturated |
| Water (pH about 7.0) | 1000 l |

4. Usefulnesses of mix-culturing of both strains

Under a condition of high temperature, mix-culturing with strain SK542 of the absolute aerobic genus Thermus will remarkably promote the decomposition and fermentation of the natural hard-decomposable organic materials which cannot be decomposed by anaerobic strain SK522.

First, the growth of strain SK542 is supplied with activated, decomposed proteins released by strain SK522. Moreover, the decomposition and fermentation of hard-decomposable organic materials in city sewage sludge, discarded wood, compost and humus, all in solid fermentation, will certainly proceed better in aerobic condition. In addition, the growth of strain SK542 in the beginning stage changes condition to a high-temperature, anaerobic condition, so that the growth of strain SK522 becomes possible in a wild condition.

(1) Solubilization of lignin

Here, the remarkable increase of lignin solubilization by strain SK522 as influenced by strain SK542 will be presented.

Hard-decomposable organic materials actually contain cellulose, lignin and other organic components which are strongly combined. Such a natural lignocellulose is actually impossible to be decomposed by strain SK522 alone.

The chemical structure of lignin is not known perfectly. However, phenylpropane which has C-3 chain in a benzene ring is a basic unit. These units are converted to a three-dimensionally randomly polymerised high molecular weight compound by radical reaction catalyzed by peroxidase. This structure is extremely resistant to microbial decomposition. Most researchers and technicians know this problem very well.

In this case, by using strain SK522, even though the process proceeds weakly or slightly weak, lignin is expected to be solubilized. Moreover, by mix-culturing with strain SK542, for example, more than 50% of rice straw lignin can be solubilized in approximately 10 days. This lignin solubilization has been demonstrated for the first time.

The practical use of these important findings is that the decomposition and fermentation of humus can be accomplished quickly at high temperatures of 50°–80° C. or more.

(2) Production of yellow pigment

Yellow pigments produced by strain SK542 and other strains belonging to the genus Thermus are insoluble-type carotenoids. These yellow pigments are then decomposed by other microbes and become water-soluble, low molecular weight compounds. These compounds are then absorbed by plants, transported to appropriate position, and become good precursors. Moreover, along with fermented products of bacillus lysate and secretion, not only the enlargement of root and shoot parts will be stimulated, but also the metabolism of reproductive growth of flower bud formation, fruit set and fruit enlargement will be effected. These have been experimentally clarified in the level of molecular biology. As their practical usages grow, their usefulness, in fruit taste, luster and storage properties will soon be accelerated.

(3) Complex of microbial ecological system

By applying strain SK542 having yellow pigment, the growth of heterotrophic microbes and soil-borned microbes will be stimulated. The important thing is that in the production of humus, strain SK522 as a thermophilic microbe will not be directly activated. First, the normal-temperature heterotrophic microbes are increased, and the heat of fermentation is accumulated, resulting in an increase of temperature. However, individual strain of the thermocellulolytic bacteria and a few bacteria alone do not work in decomposition of naturally hard-decomposable organic materials. The complex of microbial flora is necessary. Each type of functioning bacteria is then increased.

During high temperature decomposition of hard-decomposable organic materials, strain SK522 is developed in the center of bacillus flora. The process of humus development does not involve simple changes in ingredient compounds. A mutual interaction among complex microbial flora and those changes is involved, and this strong relation will then continue efficiently.

Other efficient bacteria mixed with strains SK522 and SK542, are listed below.

(1) A culture of hemicellulose decomposing bacteria

Hemicellulose formes plant (cell wall) together with cellulose. They are called xylan, araban, dextran, mannan and galactan, dependent on sugar component.

The culture of hemicellulose decomposing bacteria is prepared from Iwata's medium added with about 1% of concentrated rice straw xylan, at 30°–38° C., and in a common anaerobic condition. Generally, it contains one or a mixture of more than two of *Bacterium vulgatus, B. prodigiosum, B. mesentericus rubber*, and *Microspira agerliguefaciens*.

(2) A culture of pectin decomposing bacteria

Bacteria which strongly decompose pectin are grouped into aerobic ones such as baccilus or ethanol-acetone bacteria, and anaerobic ones such as butylate bacteria.

According to the present invention, bacteria are prepared in Molish's medium. The inoculation materials are soil, compost, horse manure, bagase or decayed hemp, which are incubated at 27°–35° C. for 3–5 days as thick or thin layers, and mixed several times. The invented culture usually contains more than one strain.

(3) A culture of soil actinomycetes

Working with soil actinomycetes (Actinomycetales Buchanan, 1917) is generally difficult. However, together with other microbes, they certaintly posses a significant meaning as each organic substances, especially hard-decomposable cellulose, lignin, can be decomposed, leading to the formation of humus in soil or the production of antibiotics for microflora control.

The culture is prepared in Waksman's medium (Waksman, 1919) by inoculating with fertile soil, compost or manure.

(4) A culture of soil fungi or yeast

The place in which soil fungi exists in a large quantity is soil which contains bacteria and actinomycetes. In cultivated land which contains plant root, especially in rhizosphere, they exist in a large quantity and are vigorous. They are responsible for decomposing organic substances of plant decays and making the soil fertile. Fungi are mainly active in the early stage of decomposition.

There are a lot of uncertainties in the function of soil yeast. However, there are enough numbers of yeast, and as they are able to circulate a lot of vitamins and growth factors, together with other microbes, they surely act for soil fertility.

The soil fungi and yeast culture is prepared in Csapek and Dox's medium (Csapek and Dox, 1910). They are isolated from soil, compost or manure, and then cultured.

(5) Thermophilic baccilus culture

The bacillus is thermophilic, movile and forms endogenous spores. They are a group of bacteria which are widely distributed naturally in hay, leaf surface and soil. Their strains are strongly heat resistant. As they can even grow at temperature more than 55° C., they are important bacteria in compost production. Moreover, as they are known to secrete antibiotics, bacitracine and bacillicine, they recently have received attention from the field of soil-plant pathology. Trials in using those bacteria in crop production, as a consequence are possible, by heating a suspension from fertile soil, compost or manure at 80° C. for 10 minutes. The bacteria are then aerobically cultured in Waksman medium (Waksman, 1922) at 50°–60° C. Finally, they can be cultured as a pure or mix culture.

(6) A culture of yellow pigment producing bacteria

Yellow pigment produced by bacteria is carotenoid pigment. The bacteria are especially found both in a large quantity and kind in mature compost. They are also found in plant leaf surface. From those sources, they are isolated and then cultured in meat extract, peptone or yeast extract medium at 25°–35° C., under an aerobic condition. They are simply identified from the appearing colors of yellowish green, yellow, yellowish brown or dark red. A culture of one or more than one species of *flavobacterium, chromobacterium, pseudomonas, serratia* and phototrophic bacteria is usually obtained.

The organic material decomposing process by the bacteria is enhanced by limestone powder, dolomite powder, shell powder, powder of carapaces of crab and other sea shells, $CaCO_3$, $Ca(OH)_2$, perlite, permiculite, zeolite, powders of diatom earth and basic rock, pulverized peatmose and charcoal, alone or in combination.

Micronutrients and minerals that can be added to enhance the decomposing process are biotin, nicotinic acid amide, thiamine, pyridoxamine, vitamin $B_{12}$, vitamins of paraamino benzoic acid, arginine, cystine, glutamic acid, isoleucine, leucine, lysine, methionine, phenylalanine, threonine, triphtophane, tyrosine, amino acids of barium, iron, mangan, cobalt and microminerals of calcium. As those enhancer, micronutrients and minerals are chosen depending to existing bacteria, purposes of usage, soil conditions, topography and climate, they have to be carefully selected.

By giving a mix culture of bacteria or adding organic material decomposing agents to each organic material, the decomposition can be completed in 5–12 days at 60°–65° C. or in 7–14 days at 50°–75° C. The process is best under an aerobic condition. Eventhough each organic material responses differently, 2–5% of the mix culture can be added.

For soil improvement, the mix culture of bacteria or organic material decomposer can be applied directly to soil. Although the amount that can be applied to the soil differs according to soil types and the amount of organic materials, about 1.000 folds diluted substances in 200–1.000 liters/ha, for example 500 liters/ha, can be used.

The present invention provides new strain SK522. In addition, a mix culture of strain SK522 and SK542 is provided and promising. The synergistic effects as a result of mix-culturing strains SK522 and SK542 provide enhanced lignin decomposition and promote cellulose decomposition and other processes as well.

Strain SK522 is excellent for decomposing cellulose and able to weakly or slight-weakly solubilize lignin. Strain SK542 is absolute aerobic, thermophilic bacterium, active in a wide pH range, able to decompose and ferment protein, and produces a yellow pigment of carotenoid.

The physical and chemical properties of protein decomposing enzymes of strain SK542 are presented in the following.

TABLE 1

Physical and chemical properties of protein decomposing enzymes of strain SK542

| Properties | Enzymes | |
|---|---|---|
| | Protease A | Protease B |
| Molecular weight | 39,000–32,000 | 28,000–23,000 |
| Optimum pH | 9.5–10.0 | 7.0–7.5 |
| Usable pH range | 8.0–12.0 | 4.0–9.5 |
| Optimum temperature | 75° | 80° |
| Heat resistance (50% activity after 20 min.) | 82° | 87° |
| Substrate specificity | Haemoglobin, insulin, Casein, | In addition, keratin, |

TABLE 1-continued

Physical and chemical properties of protein decomposing enzymes of strain SK542

| Properties | Enzymes | |
|---|---|---|
| | Protease A | Protease B |
| | albumin | collagen, elastin |
| Inhibitor | DFP, EDTA | DFP, EDTA |
| Activator | — | — |

Separation: Gel filtration and Sephadex G-75

Other than proteases A and B, which seem to be novel enzymes, there are several kinds of unstable enzymes in it.

The physical and chemical properties of pigment of strain SK542 are stated as the following.

Yellow pigment produced by the strain belongs to a carotenoid group. It is insoluble in water but soluble in methanol, ethanol, petroleum ether, benzene, aceton, chloroform and mix solutions of aceton+methanol (7:3) and aceton+ethanol (1:1). It shows the highest peak in the infrared absorbance at 450 nm and small peaks at 430 and 435 nm.

Moreover, by mix-culturing both new thermophilic strains, synergistic effects can be achieved, but not additive effects, as a result of their interactions. Their function will be mutually increased and as a result, lignin, cellulose and protein can be decomposed rapidly.

As both strains are available for mix-culturing, fermenting and decomposing agents for organic materials can be produced. That fermenting and decomposing agents, corresponding to practical usages, climate, topography and soil, contain strain SK522, SK542 and other useful microbes. As a consequence, their function will be increased, and new, useful effects can be achieved.

The invented mix culture consists of the two selected bacteria, thermophilic cellulose decomposing bacteria (strain SK522) and bacillus of the genus Thermus (strain SK542), and other microbes. Corresponding to climate, topography, soil environmental conditions and cultivated plants, some microbes can be selected and mixed.

Experiments

The followings are detail explanations on the applicable experiments of the invented bacteria. However, they do not mean to give limitations on their usages.

EXAMPLE 1

Method of lignin solubilization

| 1. Bacteria: | a large amount of mix culture of strains SK522 and SK542 |
| | a large amount of culture of strain SK522 |
| | a large amount of culture of strain SK542 |

Each culture is as described in the present specification.

2. Materials: the material used in this experiment was rice straw (non-glutinous type). Its analytical data is shown in Table 2.

TABLE 2

Analytical composition of rice straw (non-glutinous)

| Fat | Sugars | Hemicellulose | Cellulose | Lignin | Crude protein | C/N |
|---|---|---|---|---|---|---|
| 1.3 | 2.2 | 15.8 | 42.7 | 17.4 | 3.3 | 64.1 |

Analysis was conducted according to the method of Kyusyu University. Crude protein=total N×6.25.

3. Experimental method

Put 10.0g of the air-dried material into a 1000 ml Erlenmeyer flask. 700 ml of medium E (non-filter paper) was carefully added, and after sterilization, a given amount of the bacteria was inoculated, and then cultured at 65° C. for 20 days.

4. Result

Percentage of lignin solubilization (%)=Weight of solubilized lignin (=lignin weight before solubilization−residual lignin weight)
×100
Lignin weight before solubilization Percentage of cellulose fermentation (%)=Weight of fermented cellulose (=cellulose weight before treatment−residual cellulose weight)
×100
Cellulose weight before treatment Percentage of protein decomposition (%)=Weight of decomposed protein (=protein weight before decomposition−residual protein weight)
×100
Protein weight before decomposition 5. Experimental Results

TABLE 3

Experimental Results

| Items | Duration | | | | | |
|---|---|---|---|---|---|---|
| | 2 days | 5 days | 10 days | 12 days | 15 days | 20 days |
| Lignin solubilization (%) | | | | | | |
| Strain 522 + Strain 542 | 25.1 | 37.3 | 54.7 | 56.1 | 60.6 | 63.7 |
| Strain 522 | 3.4 | 6.3 | 7.1 | 7.0 | 8.3 | 8.7 |
| Strain 542 | — | — | — | — | — | — |
| Cellulose fermentation (%) | | | | | | |
| Strain 522 + Strain 542 | 88.2 | 92.7 | 91.6 | 92.5 | 91.3 | 92.4 |
| Strain 522 | 10.6 | 17.6 | 20.7 | 22.3 | 21.8 | 22.0 |
| Strain 542 | — | — | — | — | — | — |
| Protein decomposition (%) | | | | | | |
| Strain 522 + Strain 542 | 48.1 | 69.0 | 74.2 | 72.9 | 73.6 | 75.4 |
| Strain 522 | 13.2 | 17.4 | 19.5 | 24.7 | 25.4 | 26.3 |
| Strain 542 | 42.3 | 44.6 | 46.0 | 46.3 | 97.4 | 47.5 |

Each measurement was an average of 3–5 replications.

As clearly shown in Table 3, in the mix culture of the thermophilic strains SK522 and 542, each effect is not additive, but is synergistic. From the natural hard-decomposable cellulosic substances of rice straw, during 10–12 days, more than 50% lignin was solubilized, more than 90% cellulose was fermented and more than 70% protein was strongly decomposed. Obvious differences from a single culture of strain 522 and strain 542, were recognized.

EXAMPLE 2

Effects of organic material decomposors on sawchip fermentation

1. Decomposor: 10% yeast extract (wt/vol) and 10% peptone (wt/vol) were added to a mix culture of strains SK522 and SK542 to prepare a decomposor
2. Material: sawchip. A cryptomeria free, 17–20 years old, was sawn into particles of 3.0–1.0 mm.

TABLE 4

| | | Composition of Sawchip (% dry matter) | | | | |
|---|---|---|---|---|---|---|
| Fats | Sugars | Hemicellulose | Cellulose | Lignin | Crude protein | C/N |
| 2.3 | 3.3 | 5.2 | 58.6 | 23.6 | 0.58 | 559.4 |

Analysis was conducted according to the method of Kyushu University. Crude protein=total N×6.25

3. Experimental Method and Result Expression

Ten grams of the air-dryed material were put into a 1000 ml Erlenmeyer flask. 700 ml of medium E (no filter paper; refer to page . . . (19)) were carefully added, and after pasteurizing, an appropriate amount of the decomposor was inoculated, and then cultured at 65° C. for 20 days. The medium was made up to compensate evaporation.

The results of lignin solubilization, cellulose fermentation and protein decomposition were calculated as in Experiment 1.

4. Experimental Result

The results are shown in Table 5.

TABLE 5

| | Experimental Results | | | | | |
|---|---|---|---|---|---|---|
| | Duration | | | | | |
| Item | 2 days | 5 days | 10 days | 12 days | 15 days | 20 days |
| Lignin solubilization (%) | 23.5 | 35.1 | 55.6 | 57.3 | 64.0 | 68.7 |
| Cellulose fermentation (%) | 84.3 | 90.3 | 92.9 | 91.5 | 92.2 | 91.5 |
| Protein decomposition (%) | 43.7 | 54.8 | 60.7 | 64.1 | 68.9 | 71.5 |

Each measurement was an average of 3–5 replications.

In about 10–12 days, the decomposor of organic material comprising as a main component a mix culture of strains SK522 and SK542 was able to solubilize more than 50% lignin of the naturally hard-decomposable cellulosic substances of sawchip. As in the case of a single culture of strain SK522, both cellulose and protein were able to be fermented and decomposed very steadily after those days.

EXAMPLE 3

Methods of powder and granular-type decomposor and compost production

1. Production of decomposor

To produce powder and granular-type decomposors, a mass culture of strains SK522 and SK542, selected micronutrients and minerals and a stabilizer of limestone powder were mixed well. The decomposor was produced according to standard procedure. The following example shows the raw materials for powder-type product. If necessary, granular-type can be produced by adding a granulator.

Composition of raw materials

| Mass culture of strain SK522 | 2 kg |
|---|---|
| Mass culture of strain SK542 | 2 kg |
| Biotin | 1 g |
| Vitamin $B_{12}$ | 1 g |
| Cystine | 5 g |
| Methionine | 10 g |
| Mangan | 10 g |
| Cobalt | 1 g |
| Yeast extract | 100 g |
| Diatomaceous soil | 50 kg |

2. Compost production

Cryptomeria bark was used as a main raw material. The fermentor of powder type was added and a conventional compost production method was used. The results are presented in the followings.

(1) Bark composition

TABLE 6

| Bark composition (% dry weight) | | | | | |
|---|---|---|---|---|---|
| Hemicellulose | Cellulose | Lignin | Total N | Ash | C/N |
| 11.6 | 40.5 | 32.8 | 0.18 | 2.3 | 295 |

| (2) Raw material composition | |
|---|---|
| Bark (pass through a 20 mm - sieve) | 1000 kg |
| Rice bran | 250 kg |
| Ammonium sulphate | 2 kg |
| Lime superphosphate (added in the second turn-over) | 20 kg |
| Decomposer | 60 kg |
| Water | about 60% |

(3) Compost loading

While the crushed bark of 1000 kg and the decomposor were being mixed well, water of about 60% was poured into them. The mixture was then loaded into a 180×180 cm wood box and covered with a vinyl sheet.

(4) Manufacturing process

The compost was loaded on May 10. Being turned over 3 times, lime superphosphate of 20 kg was added in the second turn-over, the process was completed on July 10. As the temperature rose quickly, in the 5th day of loading the temperature reached 61° C. Thereafter, the process was kept, running at more than 60° C. In the end of the 2nd turn-over, temperature reached the highest of 72° C. Thereafter, temperature gradually decreased for some times, entering the end of composting. Up to July 10, the total temperature was 4,383° C. day. That means the temperature rose 2.7°–3.2° C. per day. Table 7 shows color changes during turn-over periods according to Mansell's color chart.

TABLE 7

Color changes during the maturation of bark compost

| Periods | Color index |
| --- | --- |
| First turn-over (May 20) | 10 YR 6/5 (light yellowish brown) |
| Second turn-over (June 5) | 10 YR 3/5 (dim brown) |
| Third turn-over (June 25) | 10 YR 3/2 (dark brown) |
| After 2 months (July 10) | 10 YR 2/2 (dark brown) |

(5) Results

The results are shown in Table 8. By conventional methods, 3–6 months or more are required to complete composting process, by this method, however, bark composting process was able to be completed for 60 days. For 60 days the total day-temperature reached 4,383° C. day. Comparing to conventional methods, the temperature rose 2.7°–3.2° C. higher per day. Color changes during maturation indicated good results. Therefore, the decomposor was good enough to decompose the bark. Lately, this process has been clearly understood. All of these analytical values should meet the standards released by Japanese Bark Compost Society or National Bark Compost Industry Union.

TABLE 8

Analytical values of manufactured bark compost

| Items | Analytical values |
| --- | --- |
| Water (%) | 58.6 |
| Organic matter (%) | 72.4 |
| Total N (%) | 1.9 |
| C/N ratio | 24.4 |
| Total $P_2O_5$ (%) | 1.2 |
| Total $K_2O$ (%) | 0.4 |
| Total Cao (%) | 7.3 |
| pH | 6.8 |
| CEC | 82 me/100 g |
| Plant bioassay | no abnormality |
| Humusification (%) | 31.2 |

Plant bioassay: large white radish
Humusification: Okudashi's method was used $$\text{Humusification (\%)} = \frac{\text{total organic matter} - NH_4OH\text{-insoluble organic matter}}{\text{total organic matter}} \times 100$$

The followings clarify the effects of mix culture or decomposers in improving soil.

EXAMPLE 4

Effects of direct application of decomposor on soil improvements of verdue and agroforestry (1)

| | |
| --- | --- |
| Objective: | to study the utilities and effects of direct spreading of the decomposor to soil for decomposing rice straw |
| Decomposor: | the following raw materials with limestone powder were immediately mixed and made into powder or granule. |

The proportion of raw materials (stabilizer: per 1000 kg of limestone powder)

| | |
| --- | --- |
| Mix culture of strains SK522 and SK542 (as stated in III.3) | 4 kg |
| Culture of soil actinomycetes (as stated in III.3.3) | 2 kg |
| Culture of yellow pigment-producing microbes (as stated in III.3.6) | 2 kg |
| Yeast extract | 200 kg |
| Micronutrients (Co, B, Cu, Fe, Zn, Mo, Mn) | 200 kg |

1. Experimental method

Place: chernozen soil of Usa-shi, Oita Prefecture (2) Plant: tomato (strongly light responsive)

(3) Planting: January 15, seedling green house (4) Treatments: (per 10 ares)
 A: rice straw 1.5t, ammonium sulphate 7 kg, decomposor 80 kg
 B: rice straw 1.5t, ammonium sulphate 7 kg
 C: manure 2.0t
 D: control
 Note: treatments A–C were applied 30 days before transplanting (5) Transplanting: March 20, 2500 seedlings/10 ares (2 rows of 180×50 cm)

(6) Treatment arrangement: 10 seedlings per treatment, 2 replications (7) Pruning: 5th level of topping 2. Experimental Results and Discussion (1) Since from the appearance of first flower cluster the plants experienced continuously low temperature, the fruit sets of 2nd flower cluster in all treatments were inferior.

(2) Except for those of control, there were no differences in fruit set and the numbers of harvested fruits. However, fruit quality and yield of treatment A (fermentor added) tended to be higher than those of other treatments. Comparing to treatment C (manure treatment) the treatment A was somewhat inferior, but total number of superior fruits of treatment A was 97% and fruit weight was 18.6% higher than the treatment C.

(3) Changes of soil physic of treatment A provided good values in 3 phase-distribution and other tests. Its humusification was much higher than the treatment B (ammonium sulfate treatment).

In short, as the plants experienced low temperature during growth period, fruit sets of second flower cluster were inferior. However, they grew well, yield, fruit quality and soil physic were good, those indicated good results from a direct application of the decomposer. In other words these results demonstrated the practical uses of the decomposer.

3. Experimental data

The data are presented in Table 9 and 10.

TABLE 9

| | Yield per 10 plants (May 10–July 15) | | | | | | | |
|---|---|---|---|---|---|---|---|---|
| | Superior fruits | | Inferior fruits | | Discarded fruits | | Total | |
| Treatments | number | weight g | number | weight g | number | weight g | number | weight g |
| A (fermentor) | 158 | 42,078 | 57 | 3,084 | 57 | 3,084 | 287 | 59,837 |
| B (ammonium sulphate) | 142 | 32,170 | 68 | 15,046 | 71 | 4,600 | 281 | 51,816 |
| C (manure) | 133 | 31,055 | 77 | 23,940 | 81 | 4,978 | 291 | 59,973 |
| D (control) | 140 | 32,170 | 60 | 15,582 | 63 | 3,750 | 263 | 51,502 |
| Total | 573 | 137,473 | 277 | 69,243 | 272 | 16,412 | 1,122 | 223,128 |

Note: inferior fruits were those which were cracked, malformed and more than 100 g.

TABLE 10

| | Yield Percentage | | | | | |
|---|---|---|---|---|---|---|
| | Superior fruits | | Inferior fruits | | Discarded fruits | |
| Treatments | number % | weight % | number % | weight % | number % | weight % |
| A (fermentor) | 55.05 | 70.35 | 25.09 | 24.51 | 19.86 | 5.14 |
| B (ammonium sulphate) | 50.53 | 62.08 | 24.20 | 29.04 | 25.27 | 8.88 |
| C (manure) | 45.70 | 51.78 | 26.46 | 39.92 | 27.84 | 8.30 |
| D (control) | 53.23 | 62.46 | 22.82 | 30.26 | 23.95 | 7.28 |

EXAMPLE 5

Effects of direct application of decomposor on soil improvements of verdue and agroforestry (2)

Objective: to study the utility and effects of direct spreading of decomposor for decomposing rice straw to soil planted with wheat.

Decomposer: the following raw materials were immediately mixed and made into powder or granule Composition of raw materials (stabilizer: per 1000 kg of limestone powder)

| | |
|---|---|
| mix culture of strains SK522 and SK542 (as stated in (III).3) | 4 kg |
| Culture of yellow pigment - producing bacteria (as stated in (III) 3.(6)) | 2 kg |
| Yeast extract | 200 g |
| Micro mutrients (Co, B, Fe, Mn) | 200 g |

1. Experimental Method (1) Place: Mitagawa machi, Kanzaki-gun, Saga Prefecture
(2) Plant: 'Shirogane' wheat
(3) Treatments:

| Treatments | Rice straw | Decomposer | N |
|---|---|---|---|
| A | 400 kg/10 ares | 80 kg/10 ares | 1.6 kg/10 ares |
| B | 400 kg/10 ares | 80 kg/10 ares | 0.8 kg/10 ares |
| C | 400 kg/10 ares | 0 kg/10 ares | 1.6 kg/10 ares |
| D | 0 | 0 | 0 |

Note:

(1) The rice straw was cut into pieces of 5–6 cm long with a cutter.

(2) Before plowing, 80 kg/10 ares of cale lime were applied.

2. Cultivation Outline (1) Sowing period and rate: November 9, 8 kg/10 acres (2) Cultivation pattern: 4 rows, bed width 150 cm, row width 10 cm per row (3) Fertilizers, method (kg/10 acres)

| PO | KO | N | First fertilizer | Mid-time fertilizer | Heading-time fertilizer |
|---|---|---|---|---|---|
| 10 | 14 | 14 | 5, 6 | 4.2 | 4.2 |

Note: Period of supplementary fertilizers
Mid-time fertilizer: January 10
Heading-time fertilizer: March 5

3. Experimental Results and Discussion (1) Comparing to control (D), the sprouting periods of other treatments were 2 days late. The percent germination of control was also 7–11% higher than the other treatments.

(2) The plant heights of treatments A–C were generally low. Stalk and head numbers of treatment A were very high. The percentages of effective stalks of treatments A and B which were applied with the decomposer were also high.

(3) Differences in the periods of heading and maturation among treatments were not recognized. The yield of treatments A and B, in term of the increase of head number, was abundant. Differences in yield qualities among the treatments were not recognized.

As stated above, by applying raw rice straw to wheat, its germination period was late, its percent germination was low and its first elongation tended to be restrained. However, as the decomposer was applied and 400 g of N were added per 100 kg of rice straw, N starvation was eliminated and in the middle 10 days of February its growth was improved and its yield was increased.

Therefore, in applying rice straw, to avoid any restraining factors on yield increase, a direct spreading of the decomposer was proved to be beneficial.

4. Experimental data

The data are presented in Table 11 and 12.

TABLE 11

| | Germination and growth | | | | | | | |
|---|---|---|---|---|---|---|---|---|
| | Germination period | Percent Germination | Height (cm) | | | No. of stalk (per m²) | | Effective Stalk |
| Treatments | Month/day | % | 2/10 | 3/1 | 3/24 | 2/10 | 3/1 | 3/24 | ratio % |
| A | 12/5 | 81 | 10.2 | 13.5 | 31.8 | 232 | 587 | 844 | 70.6 |
| B | 12/5 | 78 | 10.0 | 13.2 | 31.3 | 195 | 494 | 822 | 71.4 |
| C | 12/5 | 82 | 10.9 | 12.9 | 33.4 | 214 | 554 | 816 | 65.9 |
| D | 12/3 | 89 | 11.8 | 13.6 | 35.1 | 200 | 553 | 791 | 66.2 |

TABLE 12

| | Growth and yield | | | | | | | | | | |
|---|---|---|---|---|---|---|---|---|---|---|---|
| Treatment | Heading Month/day | Maturity Month/day | Straw length cm | Head length cm | No. of Head (per m²) | Straw weight kg/a. | Brain weight kg/a. | Percent yield % | 1 l weight g | 100 grain weight g | Grade |
| A | 4/20 | 6/2 | 81 | 7.9 | 596 | 45 | 43.2 | 108 | 812 | 32.6 | I |
| B | 4/20 | 6/2 | 82 | 8.3 | 544 | 45 | 41.2 | 103 | 809 | 31.6 | I |
| C | 4/20 | 6/2 | 82 | 8.1 | 538 | 43 | 40.7 | 101 | 810 | 32.2 | I |
| D | 4/20 | 6/2 | 80 | 7.7 | 524 | 46 | 40.3 | 100 | 806 | 31.2 | I |

EXAMPLE 6

Effects of direction application of decomposor on soil improvements of verdue and agroforestry (3)

Objective: prevention on the outbreak of Fusarium vine disease in cucumber

Decomposer: the following raw materials were made into bowder or granule

Composition of raw materials (stabilizer: per 1000 kg of dolomite powder)

mix culture of strains SK522 and SK542 4 kg (as stated in (III).3)

| | |
|---|---|
| culture of soil actinomycetes (as stated in (III)3.(3)) | 2 kg |
| culture of yellow pigment producing bacteria (as stated in (III)3.(6)) | 2 kg |
| yeast extract | 200 g |
| Micrountrients (Co, B, Fe, Mn) | 200 g |

1. Experimental method (1) Vegetable: cucumber 'Asomidori'

(2) Cultivation and application: On April 21 seeds were sawn in "chaff charcoal". On April 26 the seedlings were transplanted into 4.5 cm polypots (filled with uncontaminated soil). After developing 10 leaves, on May 6 the plants were retransplanted carefully into 15 cm polypots (inoculated soil) by taking their root balls and put into the pots.

Soil used for raising the seedlings was that which has been applied with compost of 2 ton/10 ares for several years. The soil was then sterilized with methyl bromide. Table 13 shows materials used. Fertilizers were applied on April 21. The soil was then inoculated with 5% "Fusarium cultured fung" (by volume) or April 28.

(3) Experimental arrangement: each treatment was composed of 20 plants, no repetition.

2. Experimental results and discussion (1) Comparing to no-decomposor treatments (B - 1 to B - 4), the disease index number and percent dead plants of decomposor treatments (A - 1 to A - 4) were lower and Fusarium vine disease was not developed.

TABLE 13

Materials and fertilizers added

| Treatments | Items | Fermentor (g/l) | Amm. sulphate (g/l) | CDU-S555 (g/l) | Talc (g/l) | Sulphide (g/l) | 'Nigatsuchi' lime (g/l) |
|---|---|---|---|---|---|---|---|
| A - 1 | Decomposor + Ammonium sulphate | 3.0 | 1.5 | — | 1.8 | 0.6 | 0.5 |
| A - 2 | Decomposor + CDU-S555 (trademark name) | 3.0 | — | 2.0 | 1.8 | 0.6 | 0.5 |
| A - 3 | Decomposor + Amm. Sulphate + 'Nigatsuchi' lime | 3.0 | 1.5 | — | 1.8 | 0.6 | 3.0 |
| A - 4 | Decomposor + CDU-S555 | 3.0 | — | 2.0 | 1.8 | 0.6 | 3.0 |
| B - 1 | Ammonium Sulphate | — | 1.5 | — | 1.8 | 0.6 | 0.5 |
| B - 2 | CDU-S555 | — | — | 2.0 | 1.8 | 0.6 | 0.5 |
| B - 3 | Amm. Sulphate + 'Nigatsuchi' lime | — | 1.5 | — | 1.8 | 0.6 | 3.0 |
| B - 4 | CDU-S555 | — | — | 2.0 | 1.8 | 0.6 | 3.0 |

Up to the end of experiment, the percentage of dead plants in aminoniom sulphate treatment (A - 1) and CDU-S555+ 'Nigatsuchi' lime treatment (A - 4) was 10%, their inhibition effects on the disease were high and the development of the disease was slow.

(2) Concerning plant growth and the results, decomposor-added treatments (A - 1 to A - 4) were better than any no-decomposor treatments (B - 1 to B - 4).

(3) Especially, decomposor-added treatments (A - 1 to A - 4) were very effective on preventing the plants from the disease. Comparing to other decomposor-added treatments catments (A - 2, A - 3) and non-decomposor treatments (B - 1 to B - 4), ammonium sulphate treatment (A - 1) and CDU-S555 +'Nigatsuchi' lime treatment (A - 4) seemed to give better results.

(4) From the above results, the application of the decomposor was clearly effective. Especially, the effects of ammonium sulphate, CDU-S555 +'Nigatsuchi' lime and their combinations on inhibiting the disease were highly recognized.

3. Experimental data

The experimental data are presented in Table 14 and 15.

TABLE 14

Growth and soil chemical properties

| Treatments | Vine length (cm) | No. of leaf | Shoot weight (g) | pH | EC (m/cm) |
|---|---|---|---|---|---|
| A - 1 | 90.3 | 11.4 | 87 | 6.89 | 1.05 |
| A - 2 | 82.5 | 8.7 | 82 | 6.64 | 1.39 |
| A - 3 | 85.6 | 10.5 | 84 | 6.96 | 1.21 |
| A - 4 | 96.9 | 11.2 | 99 | 7.00 | 1.32 |
| B - 1 | 65.2 | 9.9 | 49 | 6.61 | 1.25 |
| B - 2 | 79.8 | 7.6 | 78 | 6.57 | 1.12 |
| B - 3 | 77.7 | 7.4 | 70 | 6.83 | 1.16 |
| B - 4 | 79.0 | 11.0 | 67 | 6.88 | 1.12 |

TABLE 15

Outbreak of Fusarium vine disease

| Treatments | Disease Index | | | Percent dead plant (%) | | |
|---|---|---|---|---|---|---|
| | 5/14 | 5/29 | 6/10 | 5/14 | 5/29 | 6/10 |
| A - 1 | 0 | 20.5 | 30.0 | 0 | 10.0 | 10.0 |
| A - 2 | 5.0 | 26.5 | 43.8 | 5.0 | 20.0 | 30.0 |
| A - 3 | 5.0 | 23.0 | 35.0 | 5.0 | 15.0 | 25.0 |
| A - 4 | 0 | 16.3 | 29.4 | 0 | 5.0 | 10.0 |

TABLE 15-continued

Outbreak of Fusarium vine disease

| Treatments | Disease Index | | | Percent dead plant (%) | | |
|---|---|---|---|---|---|---|
| | 5/14 | 5/29 | 6/10 | 5/14 | 5/29 | 6/10 |
| B - 1 | 15.0 | 25.0 | 80.0 | 15.0 | 15.0 | 50.0 |
| B - 2 | 0 | 28.8 | 50.4 | 0 | 15.0 | 35.0 |
| B - 3 | 0 | 28.0 | 48.3 | 0 | 15.0 | 44.0 |
| B - 4 | 0 | 35.6 | 55.0 | 0 | 5.0 | 35.0 |

Disease index=total of individual index×100/the highest index×sample number (20)

Index: 0 healthy
1 slightly weak
2 weak
3 very weak
5 dead

Possibilities for industrial usages

As stated before, the present invention provides a useful, new strain SK522. Besides, as a mix culture of new strains SK522 and SK542 has been successful, the next results are those that can be adopted to effect the systems of microbial flora in a natural ecology, farm ecology or be made into production.

(1) Not only a lot of natural hard-decomposable organic materials can be decomposed and not just simply digested, but a lot of useful materials can be produced.

(2) As the decomposition proceeds very fast, and stable, its productivity can be maintained, and a method of compost production can be developed.

(3) In addition, the complex process for decomposition of hard-decomposable organic materials can be easily carried out in a short time, a formula of thermophilic fast decomposition can be established in one step.

(4) By applying both strains SK522 and SK542, the formation of soil microbial flora can be healthily and vigorously activated, and the growth and function of effective bacteria responding to changes in environmental factors can be maintained.

(5) At the same time, as resistances to contamination due to miscellaneous and harmful bacteria are increased, soil-borne diseases and problems due to continuous cropping can be overcome and congested.

(6) Referring to the preceding paragraphs, as techniques of applying good quality manure and compost or direct spreadings to soil and plant leaf surface are developed, characteristics of soil physic are improved, especially plant growth is activated, fertility to support productivity is promoted.

(7) The decompositions of excreta deodorization, hard protein and sewage sludge are also effective. Those hard-decomposable celluloic substances as N sources are effectively decomposed.

Again, as confirmed by the present invention, by mix-culturing the strains, lignin is solubilized well, cellulose is decomposed, and protein is strongly decomposed. Plant materials in soil or plant materials applied to soil and animal materials are quickly fermented and decomposed. As consequences, soil fertility is increased or soil structure is improved.

Reference for the 2 deposited microorganisms under Rule 13-2

Agency: Fermentation Research Institute, Agency of Industrial Science and Technology.

Address: Higashi 1-1-3, Tsukuba-shi, Ibaragi Prefecture, Japan.

Deposition number and date:

1. FERM BP-3382. May 1, 1991
2. FERM BP-3457. Jun. 18, 1991.

I claim:

1. A composition for use in decomposing organic material containing lignin or cellulose and a culture comprising a thermocellulolytic bacterium *Clostridium thermocellum* biovar. Nov. SK522 FERM BP-345 g) capable of solubilizing lignin and fermenting cellulose excellently, having a growth temperature limit of 40°–80° C., and a growth optimum temperature of 65°–72° C.

2. The composition according to claim 1 further comprising at least one additional component selected from the group consisting of vitamins, amino acid providing micronutrients and minerals in amounts effective for the growth of said bacterium.

3. A method for improving the quality of soil comprising applying to said soil the composition according to claim 2.

4. A method for improving the quality of soil comprising applying to said soil a culture of a biologically pure culture of bacterium *Clostridium thermocellum* biovar. Nov. SK522 (FRM BP -345 g) capable of solubilizing lignin and fermenting cellulose excellently, having growth temperature limit of 40°–80° C., growth optimum temperature of 65°–72° C.

5. A method for decomposing organic material comprising treating a lignin containing organic material with a mix culture of a thermocellulolytic bacterium *Clostridium thermocellum* biovar. Nov. SK522 (FERM BP-345 g) capable of solubilizing lignin and fermenting cellulose excellently, having a growth temperature limit of 40°–80° C., a growth optimum temperature of 65°–72° C. with an absolute aerobic bacterium *Thermus acquaticus* biovar. nov. SK542 (FERM BP-3382) having a growth temperature limit of 40°–82° C. in a normal concentration medium, a growth optimum temperature of 72°–76° C., and producing protein decomposing enzymes functional at a temperature range of 75°–85° C. and being active in a wide pH range of 4.0–1.3, and a yellow pigment of carotenoid, or an organic material decomposer containing either desirable vitamins, micronutrients of amino acid groups or minerals necessary for the growth of the previously mentioned microbes.

6. The method according to claim 5, wherein said lignin is solubilized.

7. The method according to claim 5, wherein said organic material is excreta which is deodorized during said treating step.

8. The method stated in claim 5, conducted at a temperature higher than 60° C.

9. The method according to claim 5, wherein said decomposed organic material is organic fertilizer.

10. The method according to claim 8, wherein said lignin is solubilized.

11. The method according to claim 5, wherein said organic material is excreta which is deodorized during said treating step.

12. The method according to claim 8, wherein said organic material is excreta which is deodorized during said treating step.

13. The method according to claim 10, conducted at a temperature higher than 60° C.

14. The method according to claim 13, wherein said organic material is excreta which is deodorized during said treating step.

15. The method according to claim 13, wherein said decomposed organic material is organic fertilizer.

16. A method for improvement of soil comprising applying either a mix culture of a thermocellulolytic bacterium *Clostridium thermocellum* biovar. Nov. SK522 (FERM BP-345 g) capable of solubilizing lignin and fermenting cellulose excellently, having a growth temperature limit of 40°–80° C., and a growth optimum temperature of 65°–72° C. and an an absolute aerobic *Thermus acquaticus* biovar. nov. SK542 (FERM BP-3382) having a growth temperature limit of 40°–82° C. in a normal concentration medium, a growth optimum temperature of 72°–76° C., and producing protein decomposing enzymes functional at a temperature range of 75°–85° C. and being active in a wide pH range of 4.0–11.3, and a yellow pigment of carotenoid, and the organic material decomposer containing cellulose and lignin to the soil.

17. A method for improvement of the soil comprising applying either a mix culture of a thermocellulolytic bacterium *Clostridium thermocellum* biovar. Nov. SK522 (FERM BP-345 g) capable of solubilizing lignin and fermenting cellulose excellently, having a growth temperature limit of 40°–80° C., and a growth optimum temperature of 65°–72° C. and an an absolute aerobic *Thermus acquaticus* biovar. nov. SK542 (FERM BP-3382) having a growth temperature limit of 40°–82° C. in a normal concentration medium, a growth optimum temperature of 72°–76° C., and producing protein decomposing enzymes functional at temperature range of 75°–85° C. and being active in a wide pH range of 4.0–11.3, and a yellow pigment of carotenoid, and the organic material decomposer containing either vitamins, micronutrients of amino acid groups or minerals necessary for the growth of the previously mentioned microbes to soil.

18. A thermocellulolytic bacterium *Clostridium thermocellum* biovar. Nov. SK522 (FERM BP-345 g) biologically pure culture capable of solubilizing lignin and fermenting cellulose excellently, having a growth temperature limit of 40°–80° C., a growth optimum temperature of 65°–72° C.

* * * * *